US00PP18231P2

(12) United States Plant Patent
Kobayashi

(10) Patent No.: US PP18,231 P2
(45) Date of Patent: Nov. 20, 2007

(54) POINSETTIA PLANT NAMED 'PER8603'

(50) Latin Name: *Euphorbia pulcherrima*
Varietal Denomination: PER8603

(75) Inventor: Ruth Kobayashi, Carlsbad, CA (US)

(73) Assignee: Paul Ecke Ranch, Encinitas, CA (US)

( * ) Notice: Subject to any disclaimer, the term of this patent is extended or adjusted under 35 U.S.C. 154(b) by 0 days.

(21) Appl. No.: 11/483,245

(22) Filed: Jul. 7, 2006

(51) Int. Cl.
*A01H 5/00* (2006.01)

(52) U.S. Cl. ..... Plt./303

(58) Field of Classification Search ..... Plt./303
See application file for complete search history.

*Primary Examiner*—Kent Bell
(74) *Attorney, Agent, or Firm*—C. A. Whealy

(57) ABSTRACT

A new and distinct cultivar of Poinsettia plant named 'PER8603', characterized by its uniform, upright, outwardly spreading and mounded plant habit; freely branching habit; dark green-colored leaves; late season flowering response; inflorescences with pink and creamy white bi-colored flower bracts; and excellent post-production longevity.

1 Drawing Sheet

Botanical designation: *Euphorbia pulcherrima.*
Cultivar denomination: 'PER8603'.

BACKGROUND OF THE INVENTION

The present invention relates to a new and distinct cultivar of Poinsettia plant, botanically known as *Euphorbia pulcherrima* Willd., and hereinafter referred to by the name 'PER8603'.

The new Poinsettia a product of a planned breeding program conducted by the Inventor in Encinitas, Calif. The objective of the breeding program is to create new Poinsettia cultivars having flower bracts with desirable colors, uniform plant habit and excellent post-production longevity.

The new Poinsettia is a naturally-occurring branch mutation of a proprietary selection of *Euphorbia pulcherrima* Willd. identified as 5-01, not patented. The cultivar 'PER8603' was discovered and selected by the Inventor from within a population of plants of the parent selection a controlled environment in Encinitas, Calif. in December, 2002.

Asexual reproduction of the new Poinsettia by terminal vegetative cuttings in a controlled environment in Encinitas, Calif. since February, 2003, has shown that the unique features of this new Poinsettia are stable and reproduced true to type in successive generations of asexual reproduction.

SUMMARY OF THE INVENTION

The cultivar 'PER8603' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'PER8603'. These characteristics in combination distinguish 'PER8603' as a new and distinct cultivar of Poinsettia:

1. Uniform, upright, outwardly spreading and mounded plant habit.
2. Freely branching habit.

3. Dark green-colored leaves.
4. Late season flowering response; under natural season conditions, plants flower in about 9 weeks in Encinitas, Calif.
5. Inflorescences with pink and creamy white bi-colored flower bracts.
6. Excellent post-production longevity.

In side-by-side comparisons conducted in Encinitas, Calif., plants of the new Poinsettia differed from plants of the parent selection, primarily in flower bract color as plants of the parent selection had pink-colored flower bracts.

Plants of the new Poinsettia can be compared to plants of the Poinsettia cultivar Peterstar Pink, disclosed in U.S. Plant Pat. No. 9,879. In side-by-side comparisons conducted in Encinitas, Calif., plants of the new Poinsettia differed from plants of the cultivar Peterstar Pink in the following characteristics:

1. Plants of the new Poinsettia had darker green-colored leaves than plants of the cultivar Peterstar Pink.
2. Plants of the new Poinsettia flowered about a week later than plants of the cultivar Peterstar Pink grown under natural season conditions.
3. Plants of the new Poinsettia and the cultivar Peterstar Pink differed in flower bract coloration as plants of the cultivar Peterstar Pink had pink-colored flower bracts.

BRIEF DESCRIPTION OF THE PHOTOGRAPHS

The accompanying photographs illustrate the overall appearance of the new Poinsettia. These photographs show the colors as true as it is reasonably possible to obtain in colored reproductions of this type. Colors in the photographs may differ slightly from the color values cited in the detailed botanical description which accurately describe the colors of the new Poinsettia.

The photograph at the bottom of sheet comprises a side perspective view of a typical flowering plant of 'PER8603' grown in a container.

The photograph at the top of the sheet is a close-up view of a typical inflorescence of 'PER8603'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Encinitas, Calif. during the winter in a polyethylene-covered greenhouse and under conditions and practices which approximate those generally used in commercial Poinsettia production. During the production of the plants, day temperatures averaged 24° C., night averaged 19° C. and light levels were about 4,000 foot-candles. Measurements and numerical values represent averages for typical flowering plants. Single plants were grown in 16.5-cm pots and pinched one time. Plants were about 14 weeks old when the photographs and the detailed description were taken.

Botanical classification: *Euphorbia pulcherrima* cultivar 'PER8603'.

Parentage: Naturally-occurring branch mutation of a proprietary selection of *Euphorbia pulcherrima* Willd. identified as 5-01, not patented.

Propagation:

*Type.*—Terminal vegetative cuttings.

*Time to initiate roots.*—About ten days at 20° C. to 22° C.

*Time to produce a rooted young plant.*—About four weeks at 20° C. to 22° C.

*Root description.*—Fibrous; white in color.

Plant description:

*Plant habit and form.*—Uniform, upright, outwardly spreading and mounded plant habit; inverted triangle. Inflorescences positioned above the foliar plane. Moderately vigorous growth habit.

*Plant height.*—About 24 cm.

*Plant diameter or spread.*—About 38 cm.

*Lateral branch description.*—Quantity: Freely branching habit, about six lateral branches develop after pinching. Length: About 18 cm. Diameter: About 4.5 mm. Internode length: About 1.7 cm. Strength: Strong. Texture: Smooth, glabrous. Color: 146B.

*Foliage description.*—Arrangement: Alternate, simple. Length: About 10 cm. Width: About 6.6 cm. Shape: Elliptic; occasionally three-pointed. Apex: Acuminate. Base: Acute. Margin: Lobed. Venation pattern: Pinnate. Texture, upper surface: Smooth, glabrous. Texture, lower surface: Minute pubescence. Surface: Rugose. Aspect: Mostly flat. Color: Developing foliage, upper surface: 147A. Developing foliage, lower surface: 147B. Fully expanded foliage, upper surface: Darker than 147A; venation, 147C. Fully expanded foliage, lower surface: 147A; venation, 147D. Petiole: Length: About 7.5 cm. Diameter: About 2 mm. Texture, upper and lower surfaces: Smooth, glabrous. Color, upper and lower surfaces: 146C.

Inflorescence description:

*Inflorescence type and habit.*—Inflorescences are compound corymbs of cyathia with colored flower bracts subtending the cyathia. One inflorescence per lateral branch. Flowers are not fragrant. Flowers persistent. Inflorescences positioned above the foliage.

*Natural flowering season.*—Autumn/winter; inflorescence initiation and development is induced under long nyctoperiod conditions. Late season flowering; response time, about 9 weeks; natural season flowering maturity date is early December for plants grown in Encinitas, Calif.

*Post-production longevity.*—Excellent post-production longevity; plants of the new Poinsettia maintain good substance and bract color for about four weeks under interior conditions.

*Inflorescence size.*—Diameter: About 25 cm. Height (depth): About 3.5 cm.

*Flower bracts.*—Quantity per inflorescence: About 18. Length, largest bracts: About 11.5 cm. Width, largest bracts: About 8 cm. Shape: Elliptic or occasionally three-pointed. Apex: Acuminate. Base: Acute to attenuate. Margin: Entire or with three points. Texture, upper and lower surfaces: Smooth, glabrous. Surface: Initially rugose, becoming smooth with development. Aspect: Initially upright to eventually flat. Venation pattern: Pinnate. Color: Developing or transitional bracts, upper surface: Centers, 50C; towards the margins, 5C. Developing or transitional bracts, lower surface: Centers, 50B; towards the margins, 1D. Fully developed bracts, upper surface: Centers, 50C; towards the margins, 5D. Centers becoming closer to 50D with development. Fully developed bracts, lower surface: Centers, 50B to 50C; towards the margins, 4C. Venation, upper and lower surfaces: Similar to flower bract color. Bract petiole: Length: About 4 cm. Diameter: About 1.5 mm. Texture, upper and lower surfaces: Smooth, glabrous. Color, upper and lower surfaces: 144A.

*Cyathia.*—Quantity per corymb: About ten. Diameter of cyathia cluster: About 2 cm. Length: About 1 cm. Width: About 6 mm. Shape: Ovoid. Color, immature: 144B. Color, mature: 144C. Nectaries: Quantity per cyathium: About one or two. Size: About 2 mm by 4 mm. Color: 14A.

*Peduncles.*—Length: About 2 mm. Diameter: About 2 mm. Strength: Strong. Aspect: Upright. Texture: Smooth, glabrous. Color: 145B.

*Reproductive organs.*—Stamens: Quantity per cyathium: About ten. Anther shape: Oval; bi-lobed. Anther length: Less than 1 mm. Anther color: 8B. Amount of pollen: Scarce. Pollen color: 12A. Pistils: None observed. Seed/fruit: Seed and fruit production has not been observed.

Disease/pest resistance: Plants of the new Poinsettia have not been shown to be resistant to pathogens and pests common to Poinsettias.

Temperature tolerance: Plants of the new Poinsettia have been observed to tolerate temperatures ranging from about 15° C. to about 30° C.

It is claimed:

1. A new and distinct Poinsettia plant named 'PER8603' as illustrated and described.

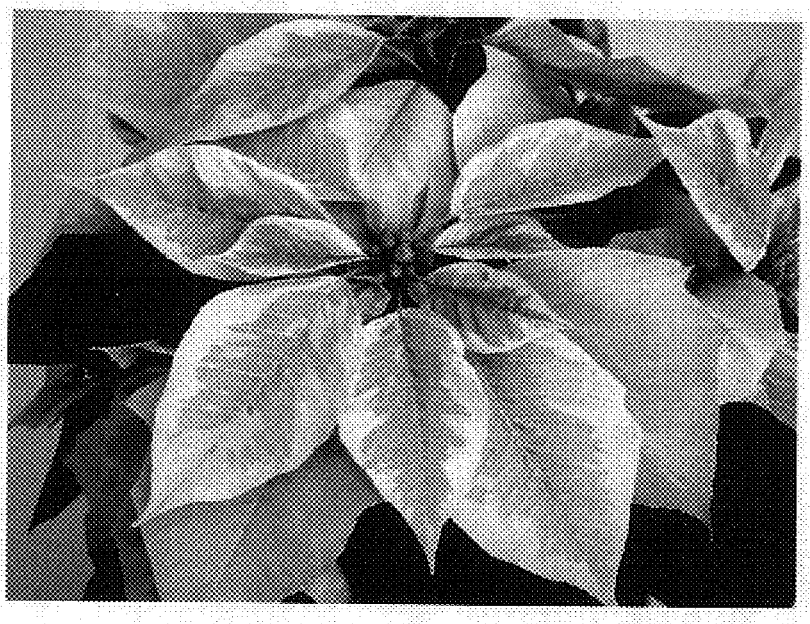
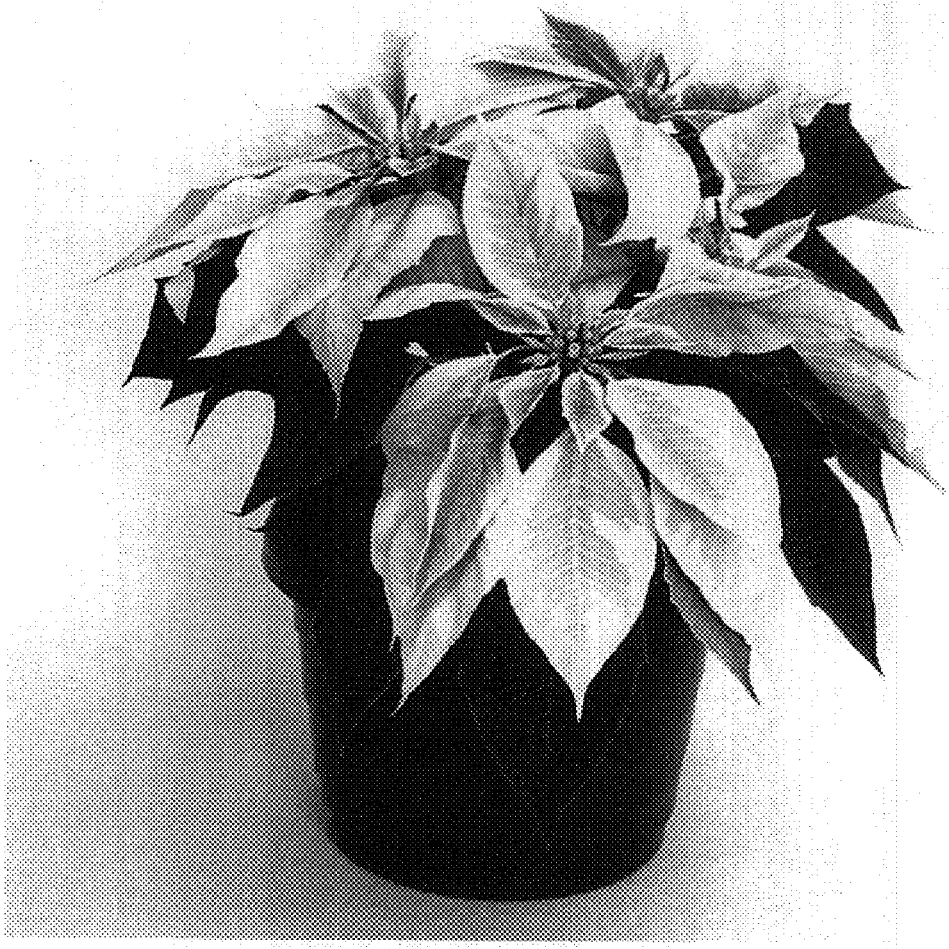

* * * * *